United States Patent
Rowe

Patent Number: 5,969,791
Date of Patent: Oct. 19, 1999

[54] INTRAOCULAR DATA DISPLAY DEVICE

[75] Inventor: T. Scott Rowe, Dana Point, Calif.

[73] Assignee: Alcon Laboratories, Inc.

[21] Appl. No.: 09/159,020

[22] Filed: Sep. 23, 1998

[51] Int. Cl.[6] ........................................ A61B 3/10
[52] U.S. Cl. ............................................... 351/205
[58] Field of Search .................................... 351/205, 245, 351/246; 600/162; 385/2, 4, 5, 27; 359/368, 656, 657, 658, 659

[56] References Cited

U.S. PATENT DOCUMENTS

| | | |
|---|---|---|
| 4,544,243 | 10/1985 | Munnerlyn . |
| 5,459,666 | 10/1995 | Casper et al. . |
| 5,499,139 | 3/1996 | Chen et al. . |
| 5,506,728 | 4/1996 | Edwards et al. . |
| 5,684,621 | 11/1997 | Downing . |

OTHER PUBLICATIONS

G. Lifante, T. Balaji, A. Muñoz-Yagüe, "Planar optical waveguides fabricted by molecular beam epitaxy of Pb-doped $CaF_2$ layers", Appl. Phys. Lett., vol. 70, No. 16, Apr. 21, 1997, pp. 2079-2081.

Boyd, "Integrated optoelectronic silicon devices for optical signal processing and communications", Optical Engineering, vol. 18, No. 1, Jan.-Feb. 1979, pp. 14-19.

Eguchi, Asano, Kannke, Ibamoto, "Selective formation of gradient-index profiles inside a planar polymer substrate by a lithographic technique", Applied Optics, vol. 33, No. 34, Dec. 1, 1994, pp. 8078-8086.

Lu, Meng, Wang, Liu, Chen, Shen, "Planar optical waveguide in Cu-doped potassium sodium strontium barium niobate crystal formed by mega-electron-volt He-ion implantation", Optics Letters, vol. 22, No. 3, Feb. 1, 1997, pp. 163-165.

Downing, Hesselink, Ralston, Macfarlane, "A Three-Color, Solid-State, Three-Dimensional Display", Science, vol. 273, Aug. 30, 1996, pp. 1185-1189.

Downing, Hesselink, Macfarlane, "A Solid-State Three-Dimensional Upconversion Display", Pro. IEEE Non-Linear Optics: Materials Fundamentals and Applications (OSA, Wash. D.C. 1994) pp. 409-411.

Shmulovich, "Er-doped glass waveguide amplifiers on silicon", SPIE, vol. 2996, pp. 143-153.

Najafi, "Overview of Nd-and Er-Doped Glass Integrated Optics Amplifiers and Lasers", SPIE vol. 2996, pp. 54-61.

Kakarantzas, Townsend and Wang, "Very Low Ion Implanted Planar Waveguides in Lead Germanate Glass", Electronics Letters v29 n 5, Mar. 4, 1993, pp. 489-490, ISSN 0013-5194.

*Primary Examiner*—George Manuel
*Attorney, Agent, or Firm*—Jeffrey S. Schira

[57] ABSTRACT

An intraocular data display device having an N×M display with each row (N) and column (M) of the display confined by a planar waveguide array. The waveguides will form uniform pixel size anywhere on the display and ensure uniform pixel luminance across the display.

7 Claims, 4 Drawing Sheets

INTRAOCULAR DATA DISPLAY DEVICE

BACKGROUND OF THE INVENTION

This invention relates generally to the field of surgery and more particularly to a data display device for microsurgery.

In many types of surgery, particularly microsurgery, the surgeon operates through an operating microscope using various electronic, pneumatic or hydraulic handpieces that are controlled by a control console. Whenever the surgeon wishes to know the operative settings of the console, the surgeon must either have an assistant read the settings, or the surgeon must look up from the operating microscope and read the settings. A device that allows the surgeon to view the console operative settings within the field of view of the microscope is desirable.

Typical operating room microscopes use an objective lens system that relays the image through the body of the microscope and reforms (focuses) the inverted image on the reticle plane of the oculars. The inverted image can, at this point, can be combined with a reticle that can be calibrated to provide measurement capability or simply qualitatively define a portion of the microscopes' field of view (FOV). The ocular eyepiece lens relays the combined image (field image plus reticle) to the observer's eye, which forms the correct (erect) image on the retina. Thus, the reticle image plane is a convenient place to add additional information to the observer's FOV.

Several prior attempts to provide intraocular or "heads-up" data displays have been made. For example, U.S. Pat. No. 4,544,243 (Munnerlyn) discloses a surgical microscope data display device that uses a cathode ray tube projector coupled to a beamsplitter mounted to the microscope between the oculars and the objective lens. While this device does project data to the surgeon, it does not project data to any surgical assistant. This device also diverts a significant portion of the image intensity away from the surgeon by the nature of the beamsplitter, eliminates the opportunity for a viewing attachment, is bulky and heavy and, thus, impractical, and does not take advantage of the inherent convenience of inserting data at the reticle image plane.

Others attempts have included eliminating the oculars and positioning the surgeon and assistant in front of a television monitor. This system permits electronic insertion of data into the display image, but the resolution, contrast, dynamic range of the image and depth perception were all degraded. In addition, these types of devices forced the surgeon to operate in a position different from his/her surgical training.

Downing and others have developed a 3-D volumetric display based on 2-step, 2-frequency upconversion fluorescence in rare-earth doped glass. Two laser beams of two different wavelengths are spatially mixed within the glass volume. The wavelengths are chosen to match the upconversion process selected (a function of the rare-earth dopant of the glass). Information within the glass volume is produced by spatially and temporarily modulating one or both laser beams. Scanning systems and modulators for each laser are electronically coordinated to produce Lissajous figures within a glass cube. Fluorescence produced by this process can be viewed at any angle. In a non-illuminated state, the glass cube is essentially clear and distortion-free. Downing also envisioned a 2-D version of this display device having a 1×N array of laser diodes addressing $N^2$ voxels, however, laser diodes intrinsically do not produce collimated beams in highly planar media. See U.S. Pat. No. 5,684,621 (Downing), the entire contents of which is incorporated herein by reference. The described 2-D device will have a highly uneven luminance distribution when uniformly raster-scanned because in one corner of the display, the beams have very short path lengths while in the opposite corner, the beams must travel the maximum path length. With rapidly diverging beams, the confluence of the beams traveling the maximum distance will produce very low or no fluorescence, as compared to the beams traveling the shortest path length, and also will produce non-uniform pixel size.

Therefore, a need continues to exist for an intraocular data display device that is positioned on the reticle image plane of a microscope ocular with no optical path modifications, uniform display intensity and with little or no loss in image intensity to the observer.

BRIEF SUMMARY OF THE INVENTION

The present invention improves upon the prior art by providing an intraocular data display device having an N×M display with each row (N) and column (M) of the display confined by intersecting planar waveguides (a planar waveguide array). The waveguide intersections will form uniform pixel size and shape anywhere on the display and ensure uniform pixel luminance across the display.

Accordingly, one objective of the present invention is to provide an intraocular data display device that fits neatly on the reticle substrate of a microscope ocular.

Another objective of the present invention is to provide an intraocular data display device having an N×M display with each row and column of the display confined by planar waveguides.

Another objective of the present invention is to provide an intraocular data display device that requires no optical path modifications.

These and other advantages and objectives of the present invention will become apparent from the detailed description and claims that follow.

DETAILED DESCRIPTION OF THE INVENTION

Figure 1:
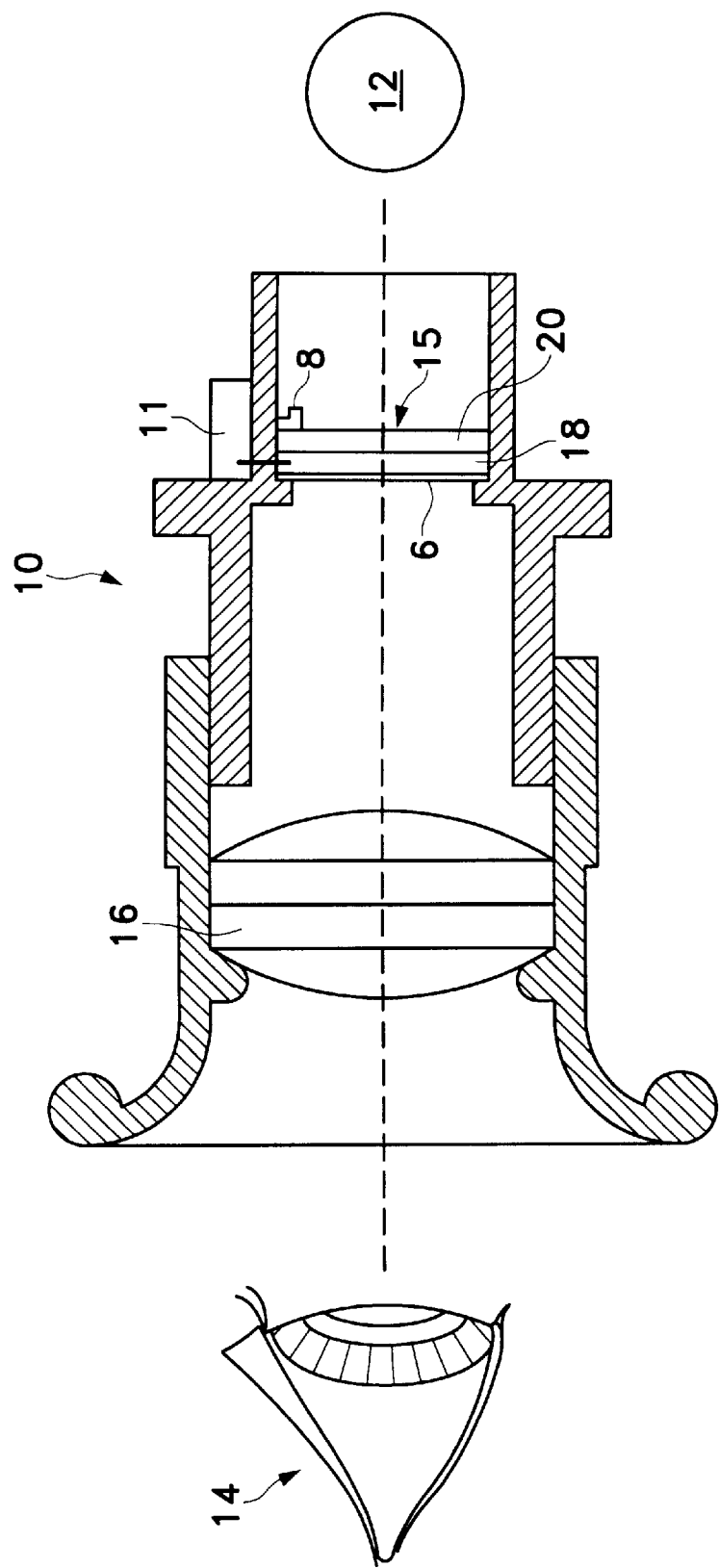
FIG. 1 is a cross-sectional view of an ocular using the display device of the present invention.
Figure 4:
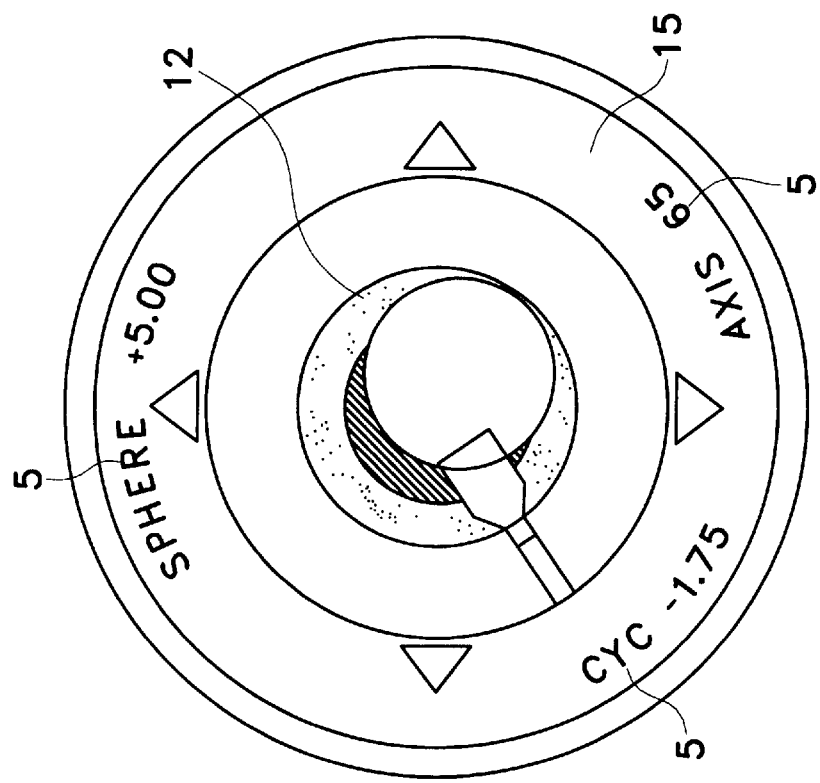
FIG. 4 is an enlarged representative view of the data display of the present invention superimposed on an image being viewed through an operating microscope.

As best seen in FIG. 1, the present invention is intended to be incorporated into ocular 10 of any commercially available operating microscope. Ocular 10 transmits image 12 coming from the objective lens system though eyepiece lens 16 so that it can be viewed by observer 14. Intraocular display device 15 of the present invention may be easily incorporated into ocular 10 at the reticle image plane where image 12 is formed in ocular 10. As best seen in FIG. 4, device 15 superimposes alphanumeric characters 5 over image 12.

Figure 2:
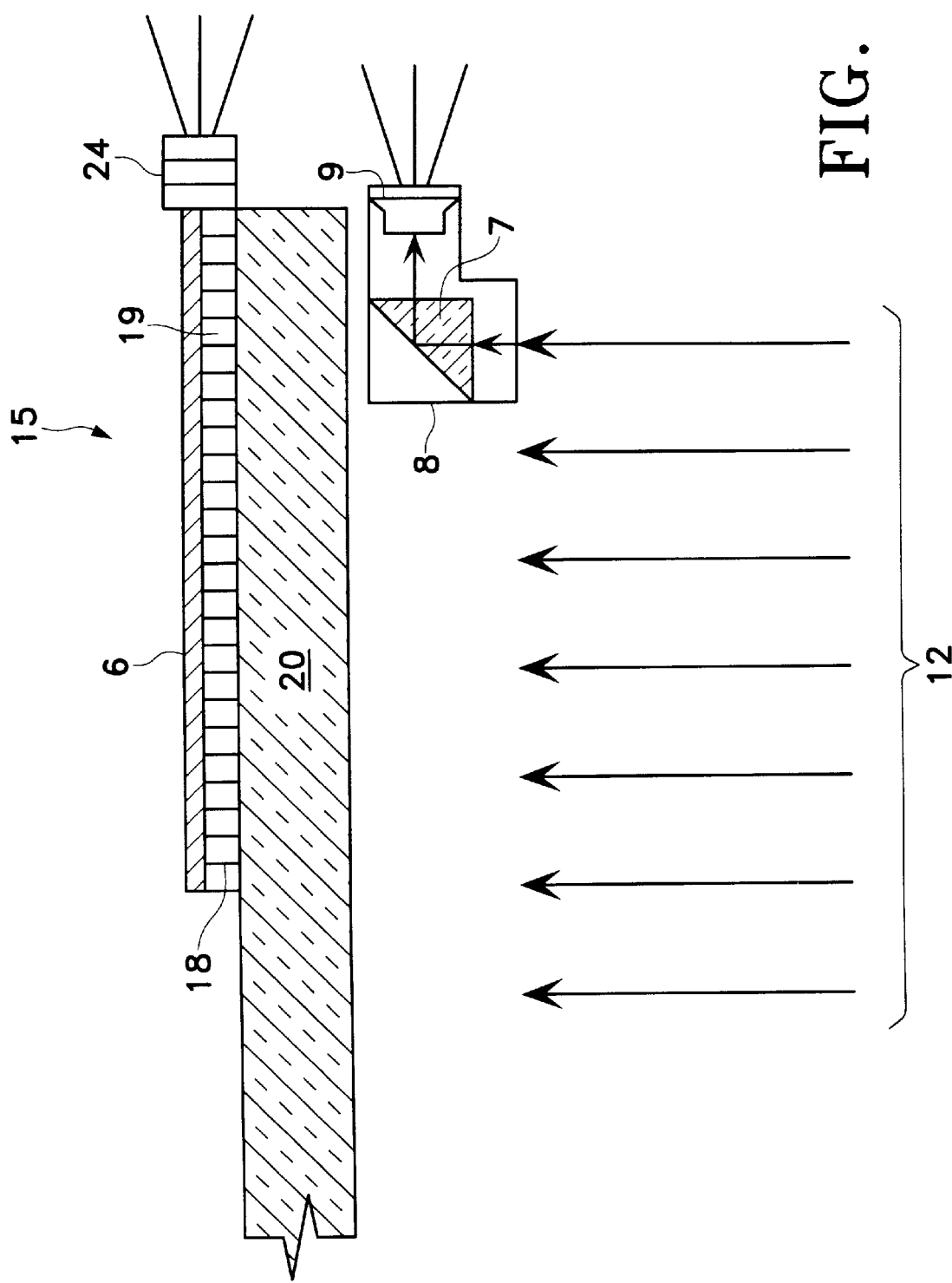
FIG. 2 is a cross-sectional view of the display device of the present invention.

As best seen in FIG. 2, display device 15 generally includes planar waveguide array 18 applied to or forming a part of substrate 20, image intensity detector 8 and coating 6. Detector 8 generally has roof prism 7 and photodiode 9. Substrate 20 may be any suitable optical quality window, such as fused silica or crown glass window. Planar waveguide array 18 may be formed in or on host material 19 by a variety of methods, well-known in the art, for example, sputtering, plasma enhanced chemical vapor deposition, flame hydrolysis, ion-exchange and sol-gel techniques may be used. Waveguide array 18 helps to confine the light from laser diode arrays 24 and 26, thus allowing the formation of a uniform pixel size and luminance where the waveguides intersect across display device 15. Suitable host materials 19 for waveguide array 18 should have a very large transparency range, with specific absorption lines lying primarily in the near infrared range due to an active ion that has been doped in small quantities into bulk transparent host material 19. Preferred host materials 19 include halide and chalcogenide glasses, such as those described in U.S. Pat. No. 5,684,621.

Figure 3:
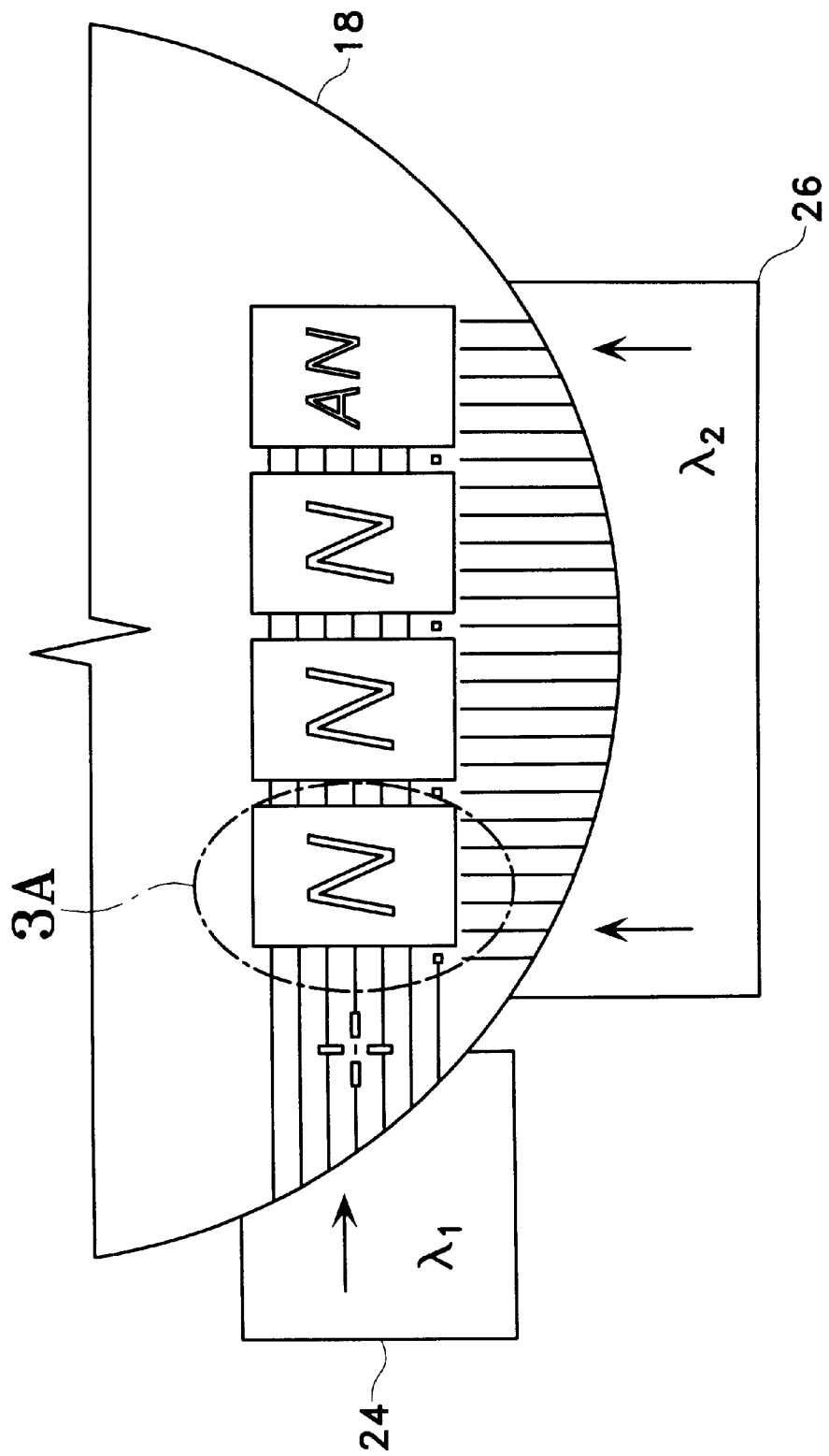
FIG. 3 is an enlarged diagram of the linear laser diode arrays used with the present invention.

As seen in FIG. 3, arranged on two side of waveguide array 18 are linear laser diode arrays 24 and 26, producing light wavelengths $\lambda_1$ and $\lambda_2$, respectively. Arrays 24 and 26 may contain any number of laser diodes, for example, array 24 may contain 7 diodes and array 26 may contain 5 diodes, each of the laser diodes in arrays 24 and 26 is arranged to correspond to a row or column of planar waveguide array 18. The output wavelengths for arrays 24 and 26 are specified to match the upconversion process selected. A two-step, two-frequency upconversion process may be used. In such a process, an active ion that has been doped in small quantities into a bulk transparent host material is optically excited to a higher energy level by absorbing energy from two different wavelengths, near-infrared laser beams at the intersection of a row and a column waveguide. The active ion, which normally occupies its lowest energy level, can absorb energy from the first laser beam $\lambda_1$ making a transition to an intermediate energy level. If the second laser beam $\lambda_2$ impinges upon the ion while it is at this intermediate energy level, the ion will absorb this energy and undergo a transition to a still higher energy level. The ion will then re-emit most of the absorbed energy as a single photon of visible light by decaying back to the ground state. See FIGS. 1 and 2 of U.S. Pat. No. 5,684,621.

Figure 3A:
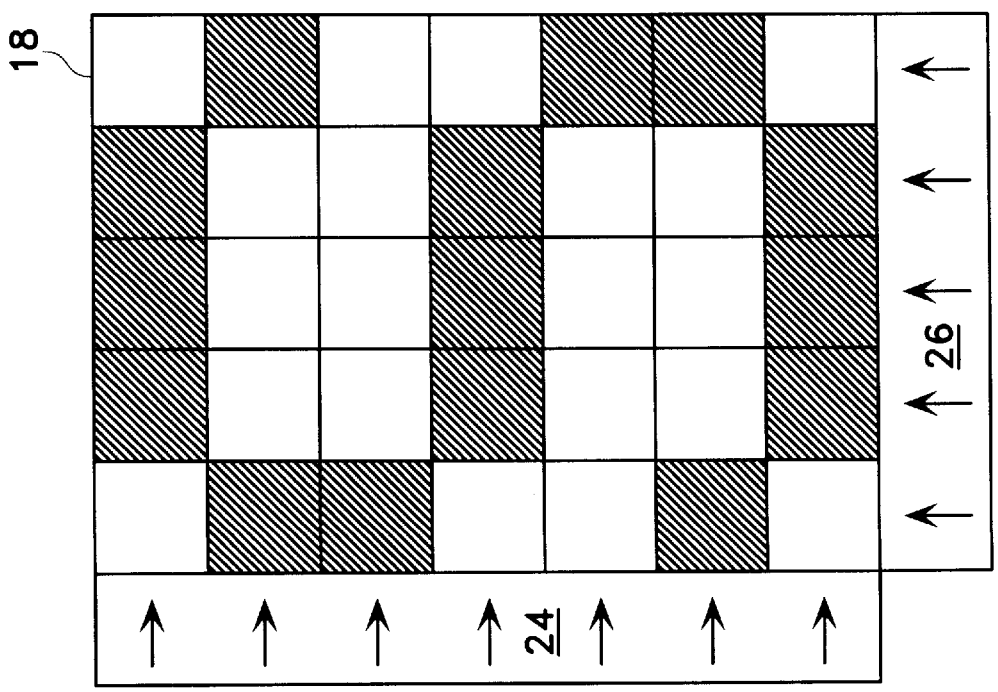
FIG. 3A is a diagram of an alphanumeric character created by the intersecting planar waveguides within the display of the present invention taken at circle 3A in FIG. 3.

In use, a row generated by an individual laser diode in diode array 24 is illuminated followed by the sequential illumination of columns by diode array 26. The selected intersection of the laser beams from array 24 and array 26 produces upconversion fluorescence (spontaneous emission) of wavelength $\lambda_3$, which is shorter in wavelength than either $\lambda_1$ or $\lambda_2$, as explained more fully in U.S. Pat. No. 5,684,621. This process is repeated for each row in a raster-scan process well-known in the art. Conventional display drivers or video electronics, well known in the art can command this process, modulating the laser beams as necessary to write information on substrate 20 through drive electronics system 11. As will be recognized by those skilled in the art, symbols and/or characters can be formed by illuminating specific pixels within display 15, as illustrated in FIG. 3A. As will also be recognized by those skilled in the art, the intensity of the laser diodes in arrays 24 and 26, shown directly adjacent to the display for clarity, will be varied so as to compensate for the varying optical path lengths across the display. Alternatively, identical diode arrays 24 and 26 can be placed on opposite sides of waveguide array 18. The use of waveguide array 18 helps create uniform pixel size and luminance across the entire display by confining the light within waveguide array 18. Dichroic shortwave-pass filter coating 6 may be applied anywhere between substrate 20 and observer 14 and reflects light of wavelengths $\lambda_1$ and $\lambda_2$, but will allow light of wavelength $\lambda_3$ to pass. Such a feature provides a means of safety to observer 14 and can be used to enhance the contrast of the display information.

Display device 15 of the present invention does not require any optical path modification to the microscope to which it is mounted and will substantially conserve surgical-field image intensity, whether illuminated or dark. Display 15 may be easily moved from one microscope to another as part of removable ocular 10. Display 15 will work well with either very dark or brightly lit images because detector 8 can be used to sample the image intensity and report to the display control electronics (not shown) to adjust the display intensity to match or exceed the image intensity.

This description is given for purposes of illustration and explanation. It will be apparent to those skilled in the relevant art that changes and modifications may be made to the invention described above without departing from its scope or spirit.

I claim:

1. A display device for use with an ocular of a microscope, comprising:
   a) a substrate;
   b) a planar waveguide array formed on or in a host material, the planar waveguide array being applied to the substrate; and
   c) a plurality of laser diode arrays arranged on at least two sides of the planar waveguide array, each of the laser diode arrays producing different wavelengths of light;
   wherein the display device is incorporated into a microscope.

2. The device of claim 1 further comprising a filter coating.

3. The device of claim 1 further comprising an image intensity detector located in the ocular between the substrate and an image being viewed.

4. The device of claim 1 wherein the host materials comprise rare earth doped halide and/or chalcogenide glasses.

5. The device of claim 1 wherein the substrate comprises an optical quality window.

6. A display device for use with an ocular of a microscope, comprising:
   a) a substrate;
   b) a planar waveguide array formed on or in a host material, the planar waveguide array being applied to the substrate;
   c) a plurality of laser diode arrays arranged on at least two sides of the planar waveguide array, each of the laser diode arrays producing different wavelengths of light and being controlled by a drive electronics system; and
   d) an image intensity detector located in the ocular between the substrate and an image being viewed;
   wherein the display device is incorporated into a microscope.

7. A method of manufacturing a display device for use with an ocular of a microscope, comprising the steps of:
   a) fabricating an array of planar waveguides on or in a host material;
   b) applying the planar waveguides to a substrate;
   c) arranging a plurality of laser diode arrays on at least two sides of the planar waveguide array, each of the laser diode arrays producing different wavelengths of light and being controlled by a drive electronics system; and
   d) locating an image intensity detector in the ocular between the substrate and an image being viewed.

* * * * *